(12) United States Patent
Viswanathan et al.

(10) Patent No.: US 7,769,428 B2
(45) Date of Patent: Aug. 3, 2010

(54) NAVIGATION OF REMOTELY ACTUABLE MEDICAL DEVICE USING CONTROL VARIABLE AND LENGTH

(75) Inventors: Raju R. Viswanathan, St. Louis, MO (US); Walter M. Blume, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1404 days.

(21) Appl. No.: 11/170,764

(22) Filed: Jun. 29, 2005

(65) Prior Publication Data

US 2006/0009735 A1 Jan. 12, 2006

Related U.S. Application Data

(60) Provisional application No. 60/583,855, filed on Jun. 29, 2004.

(51) Int. Cl.
*A61B 5/00* (2006.01)
(52) U.S. Cl. ........................ 600/424; 606/130
(58) Field of Classification Search ................. 600/424; 606/130
See application file for complete search history.

(56) References Cited

U.S. PATENT DOCUMENTS

| 6,241,671 | B1 | 6/2001 | Ritter et al. |
|---|---|---|---|
| 6,516,213 | B1 | 2/2003 | Nevo |
| 6,522,907 | B1 | 2/2003 | Bladen et al. |
| 6,534,982 | B1 | 3/2003 | Jakab |
| 6,774,624 | B2 | 8/2004 | Anderson et al. |
| 6,975,197 | B2 | 12/2005 | Creighton, IV |
| 2004/0068173 | A1 | 4/2004 | Viswanathan |
| 2004/0116803 | A1* | 6/2004 | Jascob et al. ................ 600/424 |
| 2006/0025679 | A1* | 2/2006 | Viswanathan et al. ....... 600/424 |

OTHER PUBLICATIONS

International Search Report and Written Opinion Dated: May 15, 2007 9 pages.

* cited by examiner

*Primary Examiner*—Brian Casler
*Assistant Examiner*—Amanda Lauritzen
(74) *Attorney, Agent, or Firm*—Harness, Dickey & Pierce, P.L.C.

(57) ABSTRACT

A method of navigating a medical device includes determining the location of a medical device at a point in an operating region in a subject's body, the medical device being responsive to at least one control variable to assume a desired configuration includes storing information representative of the at least one control variable being applied to the medical device at the point, and more preferably storing information representative of the at least one control variable and the device length.

9 Claims, 5 Drawing Sheets

NAVIGATION OF REMOTELY ACTUABLE MEDICAL DEVICE USING CONTROL VARIABLE AND LENGTH

CROSS REFERENCE TO RELATED APPLICATIONS

This application claims the benefit of U.S. Provisional Application No. 60/583,855, filed on Jun. 29, 2004. The disclosure of the above application is incorporated herein by reference.

BACKGROUND OF THE INVENTION

This invention relates to the navigation of remotely actuable medical devices in an operating region positioned in a subject's body.

There are a number of instances in which it is desirable to be able to determine the location of a medical device within an operating region positioned in a subject's body to facilitate navigation. Particularly in the accurate movement and positioning of a medical device it is desirable to know the current location and/or orientation of that device. Various localization systems have been developed for this purpose, including magnetic localization systems, which use electromagnetic signals transmitted to or from the medical device to determine the location of the medical device. An example of such a system is the CARTO™ XP EP Navigation and Ablation System, available from Biosense-Webster Inc. However, electromagnetic localization systems can be difficult to use where there is moving metal in or near the operating region, and can require extensive calibration. Other localization systems have been developed using ultrasound, electric potential, or image processing, however, these systems typically require that the medical device be specially constructed or adapted for use with the localization system.

SUMMARY OF THE INVENTION

The present invention relates to a method of navigating a remotely actuable medical device in a subject's body. By using information representative of at least one control variable of the remote navigation system, and preferably also the operative length of the medical device, the location of the medical device can be determined. One possible way of determining the location of a medical device is through the use of a computational model to determine the location of the device at any point based upon the at least one control variable and the operative length.

Various embodiments of the invention use the method of the present invention to determine the current location of the medical device, to return the medical device to a previous location; to identify and/or display the path taken by the medical device; to return to a path previously taken by the medical device; to characterize a surface in the operating region in the subject; and/or to create a map of a surface or a physiologic property on a surface or within a volume. These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE INVENTION

The preferred embodiment of the present invention relates to methods of navigating a remotely actuable medical device in the body, and in the preferred embodiment for navigating a medical device by determining the location of the distal tip of a remotely navigable elongate medical device. In a preferred embodiment, the remotely controllable elongate medical device is a magnetically responsive medical device that orients with an applied magnetic field. However this invention is not so limited, and applies to any remotely navigable medical device that responds to one or more applied control variables. Examples of such devices include medical devices that employ mechanical, hydraulic, pneumatic, electrostrictive/or magnetostrictive elements, or combinations thereof, to control the configuration of at least a portion of the device. The device may be any type of elongate medical device including catheters, guidewires, and endoscopes. The operative length of the device, i.e., the length of the device that can respond to the control variables, is preferably automatically controllable but could be manually controlled.

Figure 1:
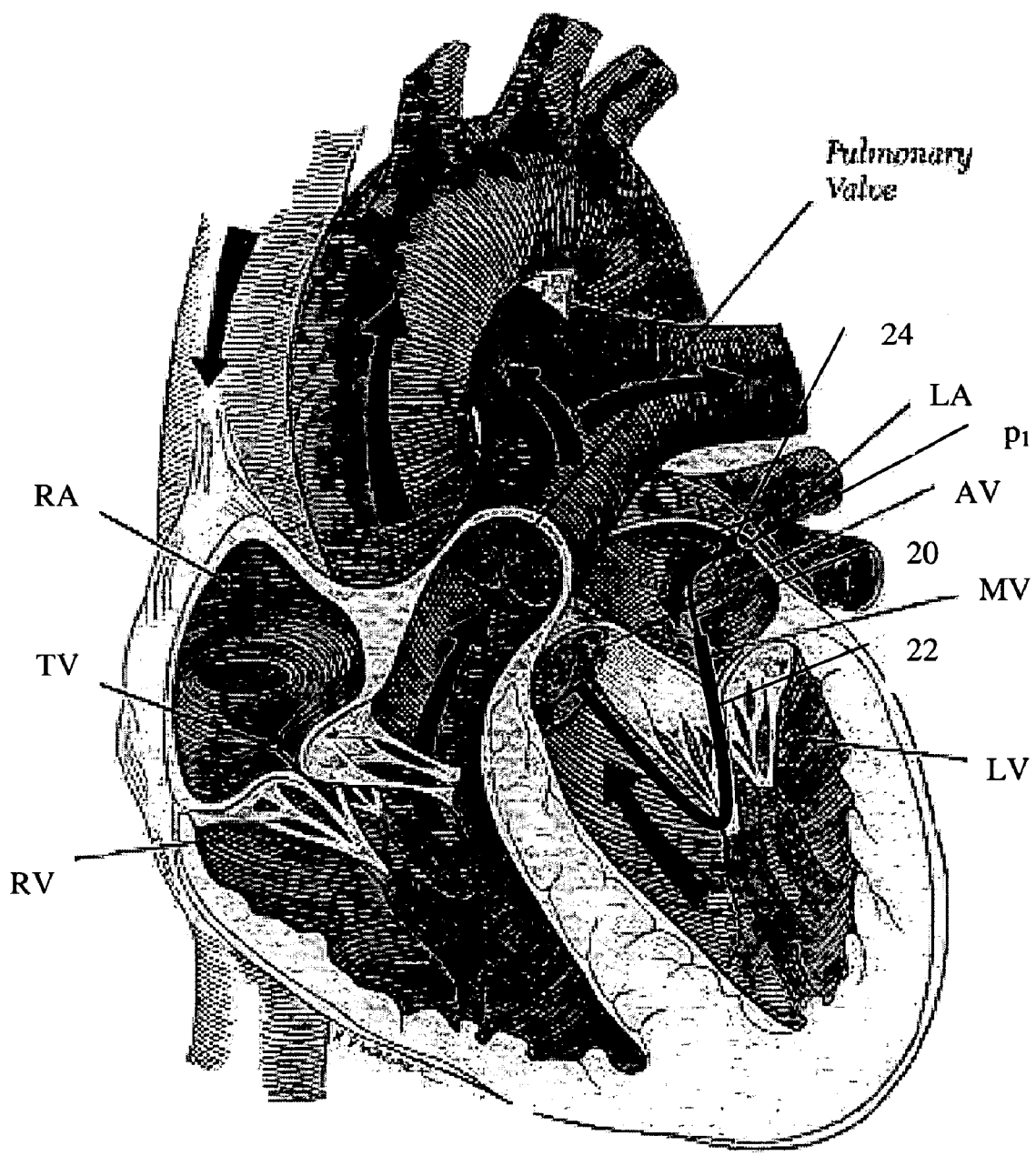
FIG. 1 is a vertical cross-sectional view of a heart, showing a catheter navigated to left atrium.

One embodiment of a method in accordance with the principles of this invention is illustrated in FIG. 1, where the distal end of a remotely navigable medical device, such as magnetically navigable catheter 20, is shown in the left atrium LA of the a subject's heart H. The distal end portion of the catheter 20 extends from the distal end of a sheath 22. In this preferred embodiment, the catheter 20 has at least one magnetically responsive element 24 adjacent its distal end. The element 24 may be a permanent magnetic material (e.g., a neodymium-iron-born (Nd—Fe—B) alloy or other suitable material) or it may be a permeable magnetic material (e.g., hiperco). The element is preferably sized and shaped to align the distal end of the catheter with an applied magnetic field less than 0.1 T, and more preferably in an applied magnetic field less than about 0.08 T. Thus, the distal end of the catheter 20 can be aligned with a magnetic field applied to the operating region in a subject, for example with one or more external source magnets. The external source magnet can be one or more permanent magnets, whose position and/or orientation can be changed to change the magnetic field applied to the operating region. An example of a suitable magnet system is disclosed in U.S. patent application Ser. No. 10/056,227, filed Jan. 23, 2002 for *Rotating and Pivoting Magnet for Magnetic Navigation*, incorporated herein by reference. The external source magnet can also be one or more electromagnets medical device, whose current can be changed to change the magnetic field applied to the operating region. An example of a suitable magnet system is disclosed in U.S. Pat. No. 6,241,671, issued Jun. 5, 2001, *Open Field System for Magnetic Surgery*, incorporated herein by reference.

As shown in FIG. 1, the distal end of the catheter 20 extends through a sheath 22 and into the left atrium LA. A magnetic field $\Im_1$ is applied to the operating region, and the catheter 20 is extended to a length $l_1$, and the distal end of the catheter 20 contacts point $p_1$. The magnetic field $\Im_1$ has at least a direction, but can also have a direction and a strength. The length $l_1$ is the free length of the device that can respond to changes in the magnet field, which in most cases is the length of the catheter 20 that projects beyond the distal end of the sheath 22. The point $p_1$ is uniquely identified by the field $\Im_1$ and the length $l_1$. In accordance with the method of this invention, the interface for controlling the magnetic field and catheter length, preferably also includes a control for storing some value representative of the magnetic field $\Im_1$, and some value representative of the catheter length $l_1$, corresponding to and uniquely identifying point $P_1$.

The distal end of the sheath 22 functions as a base or flex point for the catheter 20, so that the position and orientation of the catheter base is known by suitable identification of the sheath's distal end. If a sheath is not used, the catheter base is determined by anatomical constraints as the most distal point of support and can be identified from suitable image-based information such as X-ray imaging. While the user can control the length of the catheter manually or with an automated device, it is the free length of the catheter 20, i.e. that portion of the catheter that projects from the distal end of the sheath 22 and can respond to the control variable (e.g. the applied magnetic field in the preferred embodiment), that is important. Thus it is the control variable(s) and the free length that define the configuration of the device and, together with device base information, determine the location of the distal end. If the position of the sheath does not change, then the measure of the catheter length is a measure of the free length.

Figure 2:
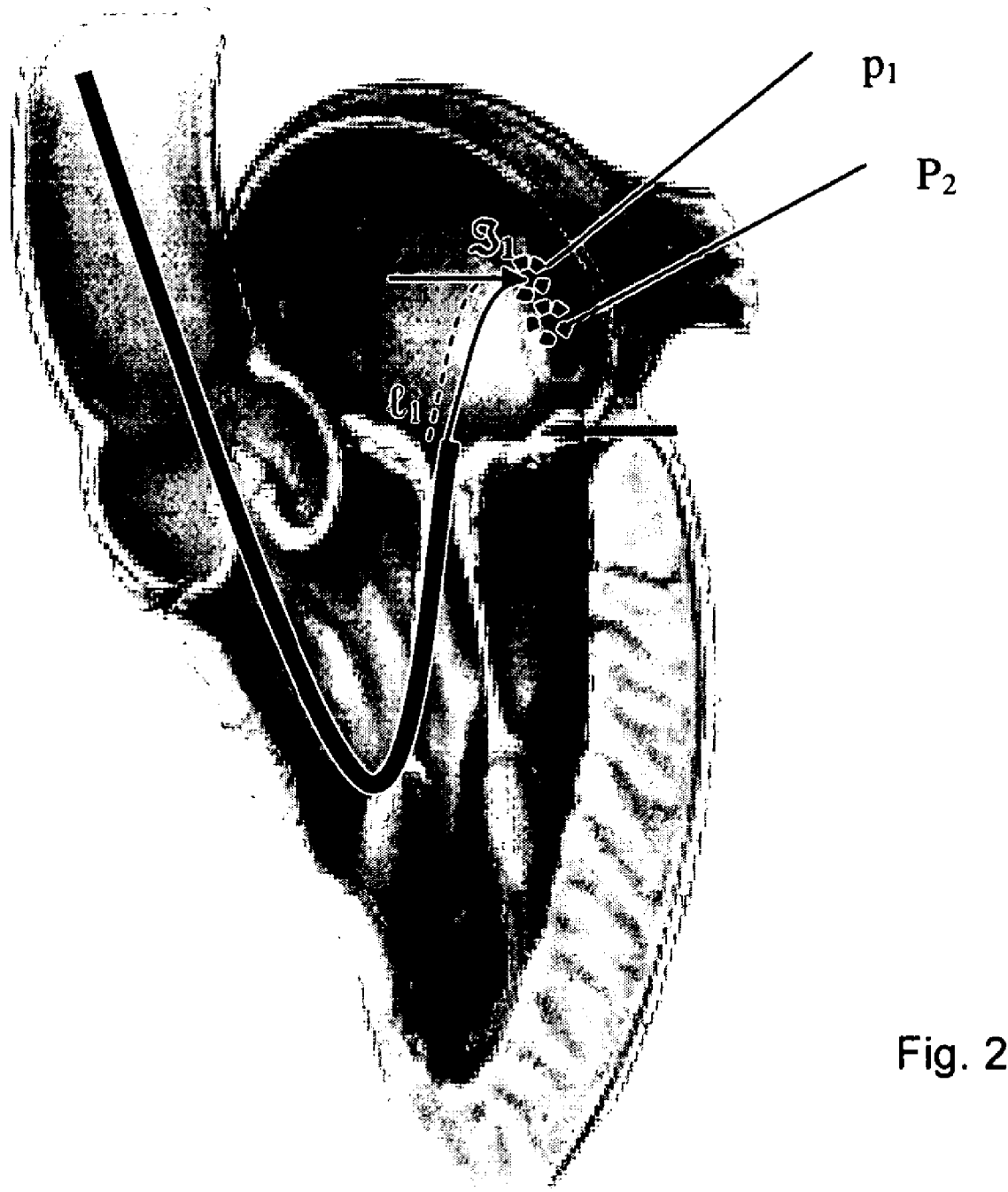
FIG. 2 is an enlarged view of the right atrium, showing the catheter

As also shown in FIGS. 1 and 2, the magnetic navigation system can be used to move the distal end of the catheter 20 to a point $p_2$ by applying a magnetic field $\Im_2$ to the operating region, and changing the length of the operating length to a length $l_2$. Again, in accordance with the method of this invention, the interface for controlling the magnet field and catheter length can include a control for storing some value representative of magnetic field $\Im_2$, and some value of the catheter length $l_1$, corresponding to and uniquely identifying point $P_2$.

The magnetic field $\Im_1$ and the length $l_1$ uniquely identify the point $p_1$ in the left atrium LA, and the magnetic field $\Im_2$ and the length $l_2$, uniquely identify the point $p_2$ in the left atrium LA, as long as the points are within the same chamber so that the device base is the same in each case. Thus, these points have been localized (uniquely identified and characterized) and this information can be used to automatically return the medical device to one of the points $p_1$ or $p_2$ by applying the appropriate magnetic field and device length. These points can also be used as part of a structure map of the surface of the right atrium LA, and additional points can be collected to provide a more detailed representation of the surface could alternatively be positions (locations and/or orientations) of the external permanent magnets. In the case of a magnetic navigation system employing one or more external electromagnets, the information could alternatively be the position and/or orientation of the electromagnets, and/or the currents in the electromagnets. Similarly, the information representative of the length can be the actual length, or some other indication of the length, for example, a position or sensor reading from an automatic device advancer. In any case the information need only be sufficient to recreate the condition so that that device can be returned to the point and/or to provide inputs to a computational model of the device so that the configuration of the device can be determined.

Figure 3:
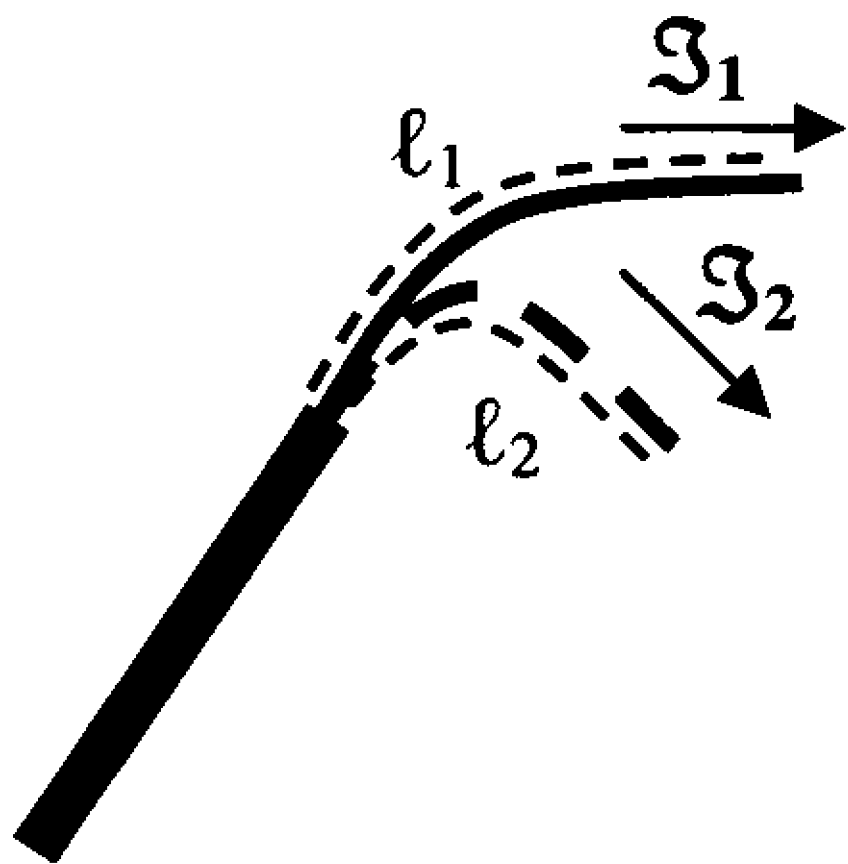
FIG. 3 is a perspective view of the distal end of the catheter, showing the catheter under the application of two different magnetic fields, while the length remains constant.

FIG. 3 illustrates the change in position achieved by a change in magnetic field from a first field $\Im_1$ to a second field $\Im_2$ while the length t of the device remains constant (i.e., $l_1=l_2$).

In an alternative implementation of the preferred embodiment, the magnetic medical device is navigable not by changing the externally applied magnetic device, but by changing the magnetic moment of the medical device in a static externally applied field. In this implementation the control variable can be one that controls or determines the magnetic moment of the medical device, including for example currents supplied to electromagnetic coils in the medical device, or any other control variables that determine the configuration of the magnetically navigated medical device. While the method has been described in the context of a magnetically navigated medical device, using information representative of the applied magnetic field and the length, this method can also apply to mechanically navigated medical devices, hydraulically navigated medical device, pneumatically controlled medical devices, electrostrictive medical devices, magnetostrictive medical devices.

In the case of mechanically navigated medical devices, the control variables may be positions of one or more push wires or pull wires, or positions of one or more gears for articulating the medical device, or any other control variables that achieve the configuration of the mechanically navigated medical device.

In the case of hydraulically navigated medical devices, the control variables may be fluid pressures in one or more hydraulic actuators, or chambers disposed in the medical device, or any other control variables that determine the configuration of the hydraulically navigated medical device.

In the case of pneumatically navigated medical devices, the control variables may be gas pressures in one or more pneumatic actuators or chambers disposed in the medical device, or any other control variables that determine the configuration of the pneumatically navigated medical device.

In the case of electrostrictive medical devices, the control variables may be voltages or currents applied to one or more electrostrictive elements or piezoelectric elements disposed in the medical device, or any other control variables that determine the configuration of the electrostrictive medical device.

In the case of magnetostrictive medical devices, the control variables may be magnetic field strength and direction applied to magnetostrictive elements in the medical device, or currents or voltages applied to electromagnetic elements in the medical device, or any other control variables that determine the configuration of the magnetostrictive medical device.

Figure 4:
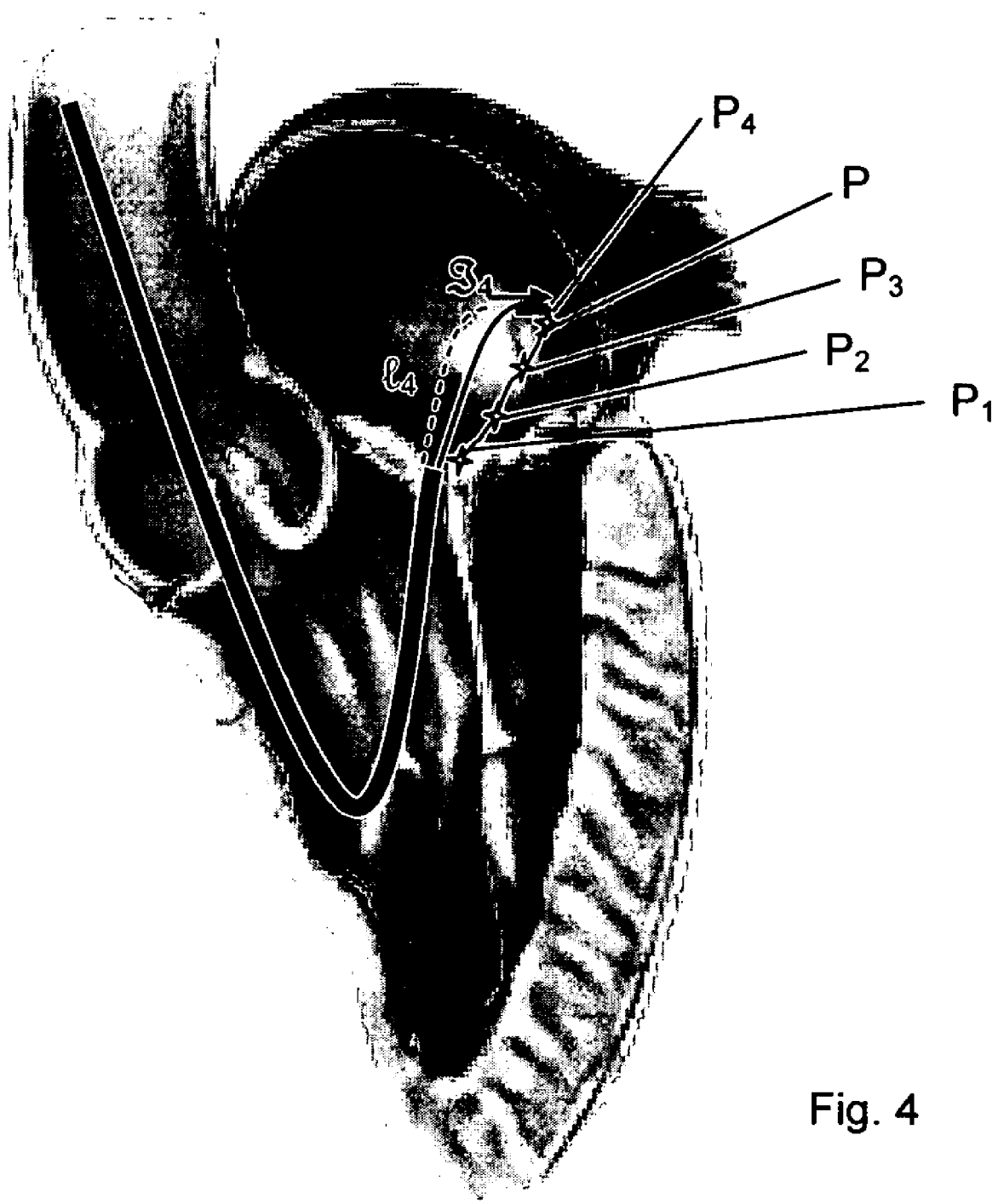
FIG. 4 is an enlarged view of the left atrium, showing a line of points.

As shown in FIG. 4, in accordance with another embodiment of this invention, a device, such as catheter 20 can be magnetically navigated along path P in the left atrium LA. Along the path P, the catheter 20 passes a plurality of points $p_1$ through $p_n$. At each point $p_x$, information representative of the magnetic field $\Im_x$ and the length $l_x$ is stored. The points $p_l$-$p_n$ can be selected by the user, or automatically selected as the catheter 20 is moved. With the points $p_l$ through $p_n$ stored, the entire path P or just a selected part of the path P can be automatically renaviagted, the navigation system using information about the field and length at each successive point in the path to automatically move the catheter 20 along the path P.

To develop a map of a surface, the catheter 20 should preferably contact the surface at each point with the same contact force. The contact force can be measured for example with a sensor on the distal tip of the catheter. The contact force can alternatively be estimated by comparing an image of the actual configuration of the catheter 20, with the predicted configuration of the catheter using a computational model.

The difference between the actual and predicted configurations is indicative of the contact force.

The information representing magnetic field and device length can be used as an input to a computational model of the medical device, i.e,. a model that predicts the configuration of the device based upon these inputs. The computational model can then be used to generate a representation of the surface containing the points. An example of such a computational model is disclosed in U.S. patent application Ser. No. 10/448,273, filed May 29, 2003, for Remote Control of Medical Devices Using a Virtual Device Interface, incorporated herein by reference.

Figure 5:
FIG. 5 is a view of the distal end of a catheter of a preferred embodiment of this invention.

As shown in FIG. 5, a catheter 100, having a plurality of strain gauges 102 thereon, is adapted for use with this methods of this invention. Each strain gauge 102 has leads 104 and 106 so that the local strain can be measured by measuring the change in voltage across the strain gauge or the change in current through the strain gauge. The catheter 100 is adapted to be configured by any means described above, for example the catheter can include one or more magnetically responsive elements, and can be configured by the application of a magnetic field; alternatively the catheter can include push wires, pull wires, gears, or other mechanical elements for configuring the catheter; alternatively the catheter can include electrostrictive (e.g piezoelectric) or magnetostrictive elements for configuring the catheter; or alternatively the catheter can include fluid or gas chambers whose pressure can be changed for configuring the catheter. However, the catheter 100 is configured, the strain gauges measure the configuration, and thus the measures from the strain gauges and the length of the device uniquely define the configuration and the location of the distal end based on a known location and orientation of the device base within an anatomical chamber of interest. By storing the measures of the strain gauges and the length, one can identify the present location of the distal end of the catheter. Since measured strain variables are derivatives of local displacements, suitable integration of the measured strain values can yield local displacements and thence the configuration of the device. This information can be used to control whatever system is used to configure the distal end of the device. Using a mathematical model of the device, the control variables required by the particular configuration system to achieve the stored measures from the strain gauges can be determined and applied if desired. Alternatively, the configuration can be repeated with a feed back system comparing the current measures from the strain gauges with the stored measures from the strain gauges. In one preferred embodiment, the strain gauges are integrated with active elements, such as piezoelectric elements, so that they both measure and cause the desired configuration. A stored voltage or current not only identifies a particular configuration, but can be used directly to recreate it.

Operation

In one embodiment of the method of this invention, the location of a magnetically orientable medical device at a point in an operating region in a subject's body is determined by storing information representative of the magnetic field being applied to the medical device at the point. A computational model of the medical device can be used to determine the location of the point, with the stored information representative of the magnetic field being applied to the medical device at the point as an input. The information representative of the magnetic field applied to the magnetically navigable device preferably includes the magnetic field direction. Where the magnetic field is applied with at least one external source magnetic, the information representative of the magnetic field applied to the magnetically navigable device can include the position of the at least one magnet, and/or the orientation of the at least one magnet, and preferably both the position and the orientation of the at least one magnet. Where the magnetic field is applied with at least one electromagnet, the information representative of the magnetic field applied to the magnetically navigable device can include the current supplied to the at least one electromagnet.

In another embodiment of the method of this invention, the location of a magnetically orientable, mechanically advanceable medical device at a point in an operating region in a subject's body is determined by storing information representative of the magnetic field being applied to the medical device at the point; and storing information representative of the free length of the medical device at the point. A computational model of the medical device can be used to determine the location of the point, with the stored information representative of the magnetic field being applied to the medical device and the stored information representative of the free length of the medical device as inputs.

In another embodiment of the method of this invention, the location of a magnetically navigable medical device at a point in an operating region in a subject's body is determined by storing information representative of the magnetic field being applied to the magnetically responsive medical device at the point and storing information about the free length of the medical device that can flex in response to an applied magnetic field, at the point.

In another embodiment of the method of this invention, the location of a medical device that has been navigated to a selected point in an operating region in a subject by applying a magnetic field to the medical device to orient the device, and mechanically advancing the medical device, is determined by storing information representative of the magnetic field being applied to the magnetically responsive medical device at the point and storing information about the free length of the magnetically navigable medical device that can flex in response to an applied magnetic field, at the point. The information representative of the magnetic field applied to the magnetically navigable device preferably includes the magnetic field direction. Where the magnetic field is applied with at least one external source magnet, the information representative of the magnetic field applied to the magnetically navigable device can include the position of the at least one magnet, and/or the orientation of the at least one magnet, and preferably both the position and orientation of the at least one magnet. Where the magnetic field is applied with at least one electromagnet, the information representative of the magnetic field applied to the magnetically navigable device can include the current supplied to the at least one electromagnet.

In another embodiment of the method of this invention, at least one location for a medical device in an operating region is stored by recording some information relating to the magnetic field applied to the medical device and some information relating to length of the medical device when the medical device is in the desired location. The information representative of the magnetic field applied to the magnetically navigable device can include the magnetic field direction. Where the magnetic field is applied with at least one external source magnetic, the information representative of the magnetic field applied to the magnetically navigable device includes the orientation of the at least one magnet, and/or the orientation of the at least one magnet, and preferably both the position and the orientation of the at least one magnet. Where the magnetic field is applied with at least one electromagnet, the information representative of the magnetic field applied to the magnetically navigable device can include the current supplied to the at least one electromagnet.

In another embodiment of the method of this invention, a surface in an operating region in a subject's body can be characterized using a magnetically navigable device by (a) navigating a magnetically navigable device by applying a magnetic field to the device and changing the free length of the device to bring the device into contact with a point on the surface; and (b) recording the point by storing information representative of the magnetic field applied to the device and the free length of the device to cause the device to contact the surface at the point; and repeating steps (a) and (b) for a plurality of points on the surface. A computational model of the device can be used to generate and render the surface, with the stored information representative of the magnetic field applied to the device and the free length of the device for each of the plurality of points as inputs. More specifically, a computation model of the magnetically navigable device and the stored information representative of the magnetic field applied to the magnetically navigable device can be used to determine the locations of the points, and displaying an image of the points.

In another preferred embodiment of the method of this invention, a method of displaying a structural map of a surface in an operating region in a subject's body is displayed using a magnetically orientable device by magnetically navigating the medical device and mechanically advancing and retracting the magnetically orientable device to a plurality of points on the surface; storing information representative of the magnetic field being applied to the magnetically orientable medical device at each point; and storing information representative of the free length of the magnetically orientable device at each point.

A computational model of the magnetically orientable device can be used to determine the location of each point based upon of the magnetic field being applied to the magnetically orientable medical device at a point and information representative of the free length of the magnetically orientable device at the point. A plurality of the points can be displayed to represent the surface.

In another embodiment of the method of this invention, a physiological map of a portion of an operating region in a subject's body can be made using a magnetically navigable device, the method comprising: magnetically navigating the device to a plurality of points in the operating region; storing information representative of the magnetic field being applied to the magnetically responsive device at each of the plurality of points; storing information about the free length of the magnetically navigable device at each of the plurality of points; measuring the value of some physiological property at each of the plurality of points. A plurality of these points and their respective physiological properties can be displayed to display a physiological map.

A computational model of the magnetically navigable device can be used to determine the location of each of the points based upon the stored information representative of the magnetic field being applied at the point, and the free length of the device at the point. The plurality of the points can then be displayed to represent the surface of the surface, together with some indication of the measured physiologic property at each point.

In another embodiment of the method of this invention, a surface in an operating region in a subject's body is automatically characterized using a magnetically navigable device by automatically navigating a magnetically navigable device by applying a magnetic field to the device to bring the device into contact with a plurality of points in predetermined relation on the surface and recording each point by storing information representative of the magnetic field applied to the device to cause it to contact the surface at the point. The step of automatically navigating preferably also includes adjusting the free length of the medical device, and wherein the step of recording each point preferably includes the step of recording the free length of the magnetically navigable device at each point. The information representative of the magnetic field applied to the magnetically navigable device preferably includes the magnetic field direction.

Where the magnetic field is applied with at least one external source magnet, the information representative of the magnetic field applied to the magnetically navigable device can include the position of the at least one magnet, and/or the orientation of the at least one magnet, preferably both the position and orientation of the at least one magnet. Where the magnetic field is applied with at least one electromagnet, the information representative of the magnetic field applied to the magnetically navigable device can include the current supplied to the at least one electromagnet.

In another embodiment of the method of this invention, a magnetically navigable medical device is navigated to return to a point to which the medical device had previously been magnetically navigated by storing information representative of the magnetic field applied to the medical device when the device was at a selected point, and using the stored information representative of the magnetic field to apply the same magnetic field to the medical device to return the medical device to the selected point. The method preferably further comprises storing information representative of the free length of the medical device when the device was at the selected point, and using the stored information representative of the free length to change the free length of the medical device to return the medical device to the selected point. The information representative of the magnetic field applied to the magnetically navigable device can include the magnetic field direction.

Where the magnetic field is applied with at least one external source magnet, the information representative of the magnetic field applied to the magnetically navigable device can include the position of the at least one magnet, and/or the orientation of the at least one magnet, and preferably both the position and orientation of the at least one magnet. Where the magnetic field is applied with at least one electromagnet, the information representative of the magnetic field applied to the magnetically navigable device can include the current supplied to the at least one electromagnet.

In another embodiment of the method of this invention, the path through a volume in a subject's body taken by a magnetically navigable medical device is recorded by applying a magnetic field to the magnetically navigable medical device to navigate the medical device along a path through the volume in the subject's body; and, storing information representative of the magnetic field applied to the medical device at each of a plurality of points along the path. The method preferably further comprises adjusting the length of the medical device to navigate the medical device along the path through the volume in the subject's body and storing information representative of the length of the medical device at each of the plurality of points for which information about the magnetic field is stored.

In another embodiment of the method of this invention, a magnetically navigable medical device is navigated substantially along a previously traversed path through a volume in a subject's body by applying a magnetic field to the magnetically navigable medical device to navigate the medical device along a path through the volume in a subject's body; storing information representative of the magnetic field applied to the medical device at each of a plurality of points along the path and subsequently navigating the magnetically navigable medical device substantially along the previously traversed path by successively applying to the magnetically navigable medical device, a magnetic field corresponding to the magnetic field previously applied to the medical device at the same point in the path. The method preferably further comprises controlling the length of the medical device to navigate the medical device along a path through the volume; storing information about the length of the medical device at each of the plurality of points at which information representative of the magnetic field was stored; and wherein the step of subsequently navigating the magnetically navigable medical device substantially along the previously traversed path includes successively controlling the length of the medical device to the length at the same point in the path.

In another embodiment of the method of this invention, a path through a volume in a subject's body taken by a magnetically navigable medical device, is displayed by applying a magnetic field to the magnetically navigable medical device to navigate the medical device along a path through the volume in the subject's body; storing information about the magnetic field applied to the medical device at each of a plurality of points along the path; determining the location of at least some of the plurality of points using a computational model of the magnetically navigable medical device and the stored information about the magnetic field applied to each point; and displaying the path as a series of points. The method preferably further comprises controlling the length of the medical device to navigate the medical device along a path through the volume; storing information about the length of the medical device at each of the plurality of points at which information representative of the magnetic field was stored; and wherein the step of determining the location of at least some of the plurality of points comprises using the computational model with information representative of the length of the medical device at each point.

In another embodiment of the method of this invention, the location of a medical device at a point in an operating region in a subject's body is determined. The medical device is responsive to at least one control variable to assume a desired configuration, and the location is determined by storing information representative of the at least one control variable being applied to the medical device at the point. The method preferably employs a computational model of the medical device and the stored information representative of the at least one control variable being applied to the medical device at the point to determine the location of the point.

In another embodiment of the method of this invention, the location of a medical device in an operating region in a subject's body is determined. The medical device is responsive to at least one control variable to assume a desired configuration, and is mechanically advanceable, and the location is determined by storing information representative of the control variable being applied to the medical device at the point; and storing information representative of the free length of the medical device at the point. A computational model of the medical device can be used to determine the location of the point using the stored information representative of the at least one control variable being applied to the medical device and the stored information representative of the free length of the medical device.

In another embodiment of the method of this invention, the location of a medical device at a point in an operating region in a subject's body is determined. The medical device is responsive to at least one control variable to assume a desired configuration. The location is determined by storing information representative of the magnetic field being applied to the magnetically responsive medical device at the point; and storing information about the free length of the medical device that can flex in response to an applied magnetic field, at the point.

In another embodiment of the method of this invention, the location of a medical device that has been navigated to a selected point in an operating region in a subject by applying a magnetic field to the medical device to orient the device, and mechanically advancing the medical device is determined by storing information representative of the at least one control variable being applied to the magnetically responsive medical device at the point; and storing information about the free length of the medical device at the point.

In another embodiment of the method of this invention, at least one location for a medical device in an operating region, is stored by recording some information relating to a control variable applied to the medical device and some information relating to length of the medical device when the medical device is in the desired location.

In another embodiment of the method of this invention, a surface in an operating region in a subject's body is characterized using a remotely navigable device. The device is responsive to at least one control variable to assume a desired configuration, and the surface is characterized by (a) navigating a remotely navigable device by applying a control variable to the device to bring the device into contact with a point on the surface; (b) recording the point by storing information representative of the at least one control variable applied to the device to cause it to contact the surface at the point; and repeating steps (a) and (b) for a plurality of points on the surface. A computational model of the remotely navigable device can be used to determine the location of the point with the stored information representative of the control variable applied to the remotely navigable device as an input. The free length of the medical device is preferably also recorded at each point.

In another embodiment of the method of this invention, a structural map of a surface in an operating region in a subject's body is displayed using a remotely orientable device. The device is responsive to at least one control variable to assume a desired configuration, and the surface is displayed by remotely orienting the medical device and mechanically advancing and retracting the remotely orientable device to a plurality of points on the surface; storing information representative of the control variable being applied to the remotely orientable medical device at each point; and storing information representative of the free length of the remotely orientable device at each point. A computational model of the device is used to determine the location of each point based upon of the control variable being applied to the remotely orientable medical device at a point and information representative of the free length of the remotely orientable device at the point. The plurality of points are then displayed to represent the surface.

In another embodiment of the method of this invention, a physiological map of a portion of an operating region in a subject's body is made using a remotely navigable device. The medical device is responsive to at least one control variable to assume a desired configuration, the map is made by applying the at least one control variable to navigate the device to a plurality of points in the operating region; storing information representative of the control variable being applied to the remotely navigable device at each of the plurality of points and storing information about the free length of the remotely navigable device at each of the plurality of points; measuring the value of some physiological property at each of the plurality of points. A computational model of the remotely navigable device can be used to determine the location of each of the points based upon the stored information representative of the at least one control variable being applied at the point, and the free length of the device at the point.

In another embodiment of the method of the invention, a surface in an operating region in a subject's body is automatically characterized using a remotely magnetically navigable device. The medical device is responsive to at least one control variable to assume a desired configuration, and the surface is characterized by automatically navigating a remotely navigable device by applying at least one control variable to the device to bring the device into contact with a plurality of points in predetermined relation on the surface and recording each point by storing information representative of the at least one control variable applied to the device to cause it to contact the surface at the point. Automatically navigating preferably includes adjusting the free length of the medical device, and wherein the step of recording each point preferably includes recording the free length of the remotely navigable device at each point.

In another embodiment of the method of this invention, a remotely navigable medical device is navigated to return to a point to which the medical device had previously been navigated. The medical device being responsive to at least one control variable to assume a desired configuration, and the device is navigated by storing information representative of the at least control variable applied to the medical device when the device was at a selected point, and using the stored information representative of the at least control variable to apply the same at least one control variable to the medical device to return the medical device to the selected point. The method preferably also includes storing information representative of the free length of the medical device when the device was at the selected point, and using the stored information representative of the free length to change the free length of the medical device to return the medical device to the selected point.

In another embodiment of the method of this invention, a path through a volume in a subject's body taken by a remotely navigable medical device is recorded by applying at least one control variable to the remotely navigable medical device to navigate the medical device along a path through the volume in the subject's body; and, storing information representative of the at least one control variable applied to the medical device at each of a plurality of points along the path. The method preferably also includes adjusting the length of the medical device to navigate the medical device along the path through the volume in the subject's body; storing information representative of the length of the medical device at each of the plurality of points for which information about the at least one control variable is stored.

In another embodiment of the method of this invention, a remotely navigable medical device is navigated substantially along a previously traversed path through a volume in a subject's body. The medical device is responsive to at least one control variable to assume a desired configuration, and is navigated by applying a control variable to the remotely navigable medical device to navigate the medical device along a path through the volume in a subject's body and storing information representative of the at least one control variable applied to the medical device at each of a plurality of points along the path; subsequently navigating the remotely navigable medical device substantially along the previously traversed path by successively applying to the remotely navigable medical device, at least one control variable corresponding to the at least one control variable previously applied to the medical device at the same point in the path. The method preferably includes controlling the length of the medical device to navigate the medical device along a path through the volume; storing information about the length of the medical device at each of the plurality of points at which information representative of the at least one control variable was stored; and successively controlling the length of the medical device to the length at the same point in the path.

In another embodiment of the method of this invention, a path through a volume in a subject's body taken by a remotely navigable medical device is displayed. The medical device is responsive to at least one control variable to assume a desired configuration, and its path is displayed by applying at least one control variable to the remotely navigable medical device to navigate the medical device along a path through the volume in the subject's body; storing information about the at least one control variable applied to the medical device at each of a plurality of points along the path; determining the location of at least some of the plurality of points using a computational model of the remotely navigable medical device and the stored information about the magnetic field applied to each point; and displaying the path as a series of points. The method preferably includes controlling the length of the medical device to navigate the medical device along a path through the volume; storing information about the length of the medical device at each of the plurality of points at which information representative of the at least one control variable was stored; and using the computational model with information representative of the length of the medical device at each point.

What is claimed is:

1. A method of determining the location of the distal end of a magnetically orientable medical device at a selected point in an operating region in a subject's body, the method comprising:

determining the location of a base of the magnetically orientable medical device;

navigating the distal end of the magnetically orientable medical device to a selected point in the operating region in the subject's body with a magnetic navigation system that applies a magnetic field to the magnetically orientable medical device;

storing information representative of the magnetic field being applied by the magnetic navigation system to the magnetically orientable medical device at the selected point; and determining the location of the distal end of the magnetically orientable medical device based upon the determined location of the base of the magnetically orientable medical device using a computational model of the magnetically orientable medical device and the stored information representative of the magnetic field to determine the location of the distal end of the medical device relative to the base.

2. The method according to claim 1 wherein the information representative of the magnetic field applied to the magnetically navigable device includes the magnetic field direction.

3. The method according to claim 1 wherein the magnetic field is applied with at least one external source magnetic, and wherein information representative of the magnetic field applied to the magnetically navigable device includes the position of the at least one magnet.

4. The method according to claim 1 wherein the magnetic field is applied with at least one external source magnetic, and wherein information representative of the magnetic field applied to the magnetically navigable device includes the orientation of the at least one magnet.

5. The method according to claim 1 wherein the magnetic field is applied with at least one external source magnet, and wherein information representative of the magnetic field applied to the magnetically navigable device includes the position and orientation of the at least one magnet.

6. The method according to claim 1 wherein the magnetic field is applied with at least one electromagnet, and wherein information representative of the magnetic field applied to the magnetically navigable device includes the current supplied to the at least one electromagnet.

7. A method of determining the location of the distal end of a magnetically orientable, mechanically advanceable medical device at a selected point in an operating region in a subject's body, the method comprising:
   determining the location of a base of the magnetically orientable medical device;
   navigating the distal end of the magnetically orientable medical device to a selected point in the operating region in the subject's body with a magnetic navigation system that applies a magnetic field to the magnetically orientable medical device;
   storing information representative of the magnetic field being applied by the magnetic navigation system to the medical device at the selected point;
   storing information representative of the free length of the medical device from the base to the distal end; and
   determining the location of the distal end of the magnetically orientable medical device based upon the determined location of the base of the magnetically orientable medical device using a computational model of the magnetically orientable medical device and the stored information representative of the magnetic field and representative of the free length of the medical device to determine the location of the distal end of the medical device relative to the base.

8. A method of determining the location of the distal end of a medical device in an operating region in a subject's body, the medical device being responsive to a remote navigation system operated by at least one control variable to assume a desired configuration, and being mechanically advanceable, the method comprising:
   determining the location of the base of the medical device;
   applying at least one control variable to the remote navigation system to bring the distal end of the medical device to a selected location;
   storing information representative of the at least one control variable being applied to the remote navigation system to position the distal end of the medical device at the selected location;
   storing information representative of the free length of the medical device between the base and the selected location; and
   determining the location of the distal end of the medical device based upon the determined location of the base of the medical device using a computational model of the medical device and the stored information representative of the at least one control variable and representative of the free length of the medical device to determine the location of the distal end of the medical device relative to the base.

9. A method of determining the location of the distal end of a medical device that has been navigated to a selected point in an operating region in a subject with a magnetic navigation system through the application of at least one control variable to the magnetic navigation system to cause the magnetic navigation system to apply a magnetic field to the medical device to orient the device, and mechanically advancing the medical device, the method comprising:
   determining the location of a base of the medical device;
   storing information representative of the at least one control variable being applied to the magnetic navigation system navigate the medical device to the selected point;
   storing information about the free length of the medical device from the base to the distal end; and
   determining the location of the distal end of the medical device based upon the determined location of the base of the medical device using a computational model of the medical device and the stored information representative of the at least one control variable and representative of the free length of the medical device to determine the location of the distal end of the medical device relative to the base.

* * * * *